United States Patent [19]
Cain et al.

[11] Patent Number: 5,858,642
[45] Date of Patent: Jan. 12, 1999

[54] CLOSED SYSTEM FOR PROCESSING CELLS

[75] Inventors: Shawn P. Cain, North Chelmsford; Timothy J. Perlman, Lexington; Deborah J. Deane, Orange; Claudy J-P. Mullon, Framingham, all of Mass.

[73] Assignee: W.R. Grace & Co.-Conn., Lexington, Mass.

[21] Appl. No.: 719,770

[22] Filed: Sep. 25, 1996

[51] Int. Cl.$^6$ ............................................ C12N 5/00
[52] U.S. Cl. .................... 435/2; 435/1.1; 435/325
[58] Field of Search ................... 435/325, 2, 1.1

[56] References Cited

U.S. PATENT DOCUMENTS

| | | |
|---|---|---|
| 3,328,255 | 6/1967 | Ilg . |
| 4,339,537 | 7/1982 | Sogi et al. . |
| 5,104,788 | 4/1992 | Carmen et al. . |
| 5,114,396 | 5/1992 | Unger et al. ............................ 435/325 |

FOREIGN PATENT DOCUMENTS 0 394 788 A1  10/1990  European Pat. Off. .

OTHER PUBLICATIONS

Kasai et al., Cryobiology, 30(1):1–11, 1993.
Carciero et al., Vox Sang, 49(6):373–380, 1985.
Dragani et al., Blut, 60(5):278–281, May 1990.
Ganshirt et al., Vox Sang, 26(1):66–73, 1974.
Hardeman et al., Dev. Nucl. Med., 6:17–28, 1984.
Mel'nikova et al., Probl. Gematol. Pereliv, Krovi, 26(6):9–11, 1981 (with English abstract).
Shanwell et al., Transfusion, 31(4):783–8, 1989.
Simon et al., Transfusion, 31(4):335–339, 1991.
Vesilind et al., Transfusion, 28(1):46–51, Jan.–Feb. 1988.

*Primary Examiner*—Leon B. Lankford, Jr.
*Attorney, Agent, or Firm*—Fish & Richardson P.C.

[57] ABSTRACT

The invention features a method of processing cells in a closed system that results in a suspension of cells in a transfer vessel containing a target number of cells. The number of cells in the closed vessel is determined from the cell concentration (i.e., the number of viable cells/mL) in the closed vessel and the total volume of the suspension in the closed vessel. The volume of the suspension in the closed vessel can be determined from the weight of the suspension and its density. In particular, the cells are preserved in a protective medium and are recovered substantially free of the protective medium in a closed vessel containing the known number of cells in a suspension.

14 Claims, No Drawings

CLOSED SYSTEM FOR PROCESSING CELLS

BACKGROUND OF THE INVENTION

The invention relates to a method of processing cells.

Cell processing is an important technique in biotechnology. In particular, cells can be manipulated and used for producing chemicals, degrading chemicals, or in medical devices and applications. In order to control these processes, it is important to be able to deliver a particular number of cells to the site of action.

The cells to be used in applications such as these can be preserved in a preservation medium (e.g., cryopreserved) so that they can be recovered alive for later use at the site of action. For example, mammalian cells, such as ova, spermatozoa, hepatocytes, blood stem cells, and the like, can be successfully cryopreserved. Cryopreservation techniques have been developed and improved over the last decade, allowing the cells to be recovered alive. However, it generally continues to be necessary to handle cells and cell suspensions in the open during processing (i.e., in a biological hood). For example, when the total number of cells in the suspension needs to be known, the cell suspension is generally handled in open vessels to wash and determine the total volume of the cell suspension. Handling the cell suspension in this manner can risk contamination of the cell suspension or expose the individual handling the cell suspension to potential biohazards.

SUMMARY OF THE INVENTION

The invention features a method for processing cells in a closed system, resulting in a suspension of cells in a closed vessel (referred to herein as a seeding vessel) containing a known number (e.g., target number) of cells.

In one aspect, the invention features a method of establishing a target number of cells in a closed vessel. A portion of cells suspended in a medium or saline is removed from the closed vessel to give a remaining suspension. The closed vessel has a sealable port from which the portion is removed. A total volume of the remaining suspension is determined in the closed vessel. A number of cells in the portion is counted to give a cell concentration of the remaining suspension. By multiplying the total volume and the cell concentration, a total number of cells in the remaining suspension is calculated. A number of cells in excess is calculated as the difference between the first total number of cells and the target number of cells. Finally, a portion of the remaining suspension corresponding to the number of cells in excess is removed from a sealable port of the closed vessel to give the target number of cells in the closed vessel.

In another aspect, the invention features a method of recovering preserved mammalian cells suspended in a protective medium. The method includes the steps of replacing the protective medium with a culture medium or saline to form a suspension, transferring the suspension to a closed vessel and establishing a target number of cells (e.g., mammalian cells) in the closed vessel.

In yet another aspect, the invention features a method of recovering a target number of cryopreserved mammalian cells suspended in a cryoprotective medium. The cryopreserved mammalian cells are recovered from the cryoprotective medium by thawing the cryopreserved mammalian cells suspended in the cryoprotective medium. A culture medium is added to dilute the cryoprotective medium. The mammalian cells are washed with the culture medium or saline to obtain a suspension. The suspension is transferred to a closed vessel, and a target number of cryopreserved mammalian cells is established. The closed vessel has a first sealable port and a second sealable port from which portions of the suspension are removed or additional amounts of culture medium or saline are added.

In preferred embodiments, the total volume of the remaining suspension is determined by weighing the remaining suspension in the closed volume to give a total mass of the cell suspension and dividing the total mass by a density to give the total volume.

In other preferred embodiments, the method further includes the step of adding an additional amount of the medium or saline to the remaining suspension through a sealable port of the closed vessel approximately equal to the portion of the remaining suspension removed to substantially restore the total volume.

In preferred embodiments, the mammalian cells are hepatocytes, pancreatic islets, chondrocytes, cartilage cells, neural cells, or blood cells, most preferably hepatocytes.

The cell concentration is the number of viable cells per milliliter of cell suspension.

The invention can have one or more of the following advantages. The new procedure can allow the cells to remain on the cell processor, be washed with both a culture medium, such as CEM or DMEM, and saline, if desired, and be transferred directly to a transfer vessel without having to be removed and processed in the open in a separate centrifuge and biological hood, which was required in the previously used open vessel method. Since the volume of the cell suspension was determined volumetrically, the suspension was generally exposed (i.e., open) to the environment. The closed system method makes it easier to maintain aseptic technique, thereby significantly decreasing the chances of contaminating either the cell suspension that is being manipulated, other microbiological samples, the operator, or the environment in which the cell processing is taking place.

The method results in more simple and fewer steps in the operating procedures, as well as a decreased financial cost for clinical site set-up. The method also eliminates the need for both a dedicated centrifuge external to the cell processor and biological hood in the cell processing environment. It also allows the aseptic collection of microbiological samples. The method can increase the number of different locations in which cell processing can take place. For example, the simplified method allows cell processing of preserved cells to be carried out closer to patients in need of treatment using the cells. The method also decreases the number of vessel transfers of the cell suspension and, therefore, the number of disposable containers used in each cell processing procedure and risk of contamination.

Other features and advantages of the present invention will be apparent from the following detailed description of the invention, and from the claims.

DETAILED DESCRIPTION

According to the invention, cells are processed in a closed system, resulting in a suspension of cells in a transfer vessel containing a known number (e.g., target number) of cells. The number of cells in the closed vessel is determined from the cell concentration of the suspension and the total volume of the suspension in the closed vessel. The target number of cells is reached by calculating a number of cells in excess and removing a portion of the remaining suspension corresponding to the number of cells in excess from the closed vessel. The volume in the closed vessel is preferably determined from the weight of the suspension in the closed vessel and its density. In particular, the cells are preserved in a protective medium and are recovered substantially free of the protective medium in a closed vessel containing the known number of cells in a suspension.

Without further elaboration, it is believed that one skilled in the art can, based on the description herein, utilize the present invention to its fullest extent. All publications cited herein are hereby incorporated by reference. The following specific examples are, therefore, to be construed as merely illustrative, and not limitive of the remainder of the disclosure.

Take the processing of cryopreserved porcine hepatocytes, for example. The cryopreserved porcine hepatocytes in a protective medium are recovered into a viable suspension of cells in a culture medium or saline. The number of cells that are recovered depends upon the use planned for the cells after recovery. In the case of porcine hepatocytes, approximately $5 \times 10^9$ cells are contained in the vessel for use in a bioartificial liver support system. Cryopreserved hepatocytes are described, for example, in Kasai, et al., *Cryobiology*, 30:1–11 (1993).

The protective medium is a culture medium that is supplemented with additives (e.g., the cryoprotectant) so that the cells survive the cryopreservation process. The protective medium is generally a culture medium that includes up to 15% dimethylsulfoxide (DMSO), e.g., 10%, as the cryoprotectant. Suitable culture media include, but are not limited to, Chee's essential medium (CEM), modified eagle medium (MEM), Dulbecco's modified eagle medium (DMEM), Leibowitz's medium, Waymouth's medium, and Kreb's medium. Traditional culture media can include additional components such as amino acids or mammalian sera. The culture medium can also include up to 20% fetal bovine serum. The preferred culture media for the porcine hepatocytes described herein are CEM and DMEM.

The process for thawing and washing cryopreserved hepatocytes can be accomplished using a cell processor that includes pumps and tubing for transferring liquids and a centrifuge, such as a COBE 2991 cell processor (manufactured by Cobe, Lakewood, Calif.). A flexible bag (e.g., a Baxter CRYOCYTE bag) containing the cryopreserved cells is thawed, for example, in a temperature-controlled water bath or microwave, to yield a cell suspension in the protective medium, which is then connected to the cell processor where the cell suspension is diluted with a culture medium. The dilution of the protective medium with the culture medium is known as equilibration. Equilibration effectively slowly decreases the osmolarity of the total suspending medium, which is high when it contains the cryoprotectant, and assists in removing the cryoprotectant from the cell suspension without adversely damaging the cells. After equilibration, culture medium is then added to remove even more cryoprotectant from the cells.

The cells are substantially separated from the mixture of media using the centrifuge and the cell-free medium is aspirated away from the cell pellet. At this point, the cells are essentially separated from the cryoprotectant.

The cell pellet can be washed with additional culture medium or saline. The washing fluid is added to the cells, the mixture agitated to form a cell suspension, and the cell suspension centrifuged to give a new cell pellet that has been washed. The washing step can be repeated multiple times to further remove the cryoprotectant and cell debris from the cells.

The cells in the cell pellet are then re-suspended in a transfer medium to form a transfer cell suspension. The transfer medium can be saline or a culture medium. The transfer cell suspension, being substantially free of cryoprotectant, is transferred out of the cell processor into a vessel.

The preferred vessel is a flexible bag with multiple sealable ports (e.g., a seeding vessel which formed of a PVC bag having an inlet with a spike septum port for transferring the cell suspension into the vessel and an outlet which can be used for sampling or withdrawing the suspension from the vessel). One of the multiple ports allows the liquid contained in the vessel to be sampled aseptically (i.e., without contaminating the sample). For example, the ports can be manually sealable (e.g., valves or clamps), heat sealable, or self-sealable (e.g., rubber septa). A sample of the cell suspension thus obtained can be used to count the concentration of cells (i.e., number of viable cells/milliliter) that are contained in the vessel. The cells are counted using, for example, a hemacytometer or automated cell counter.

The total volume of the transfer cell suspension in the vessel is determined gravimetrically. The transfer cell suspension and vessel are weighed using, for example, a top loading balance having a capacity of 5 kilograms and an accuracy of ±0.5 grams, and the weight of the cell suspension is obtained by subtracting the weight of the empty vessel, which was recorded previously. Using the density of the cells suspension of approximately 1 g/mL and the weight of the suspension, the total volume of the cell suspension is determined with enough accuracy to provide the total number of cells in the volume. If the number of cells is higher than desired, a weight of the cell suspension that corresponds to the number of cells in excess can be removed. The volume that is removed can then be replenished with saline, or another suitable medium, to maintain the total volume of the system. Typically, saline is replenished when greater than about 2% of the volume is removed (e.g., 20 mL of a total 1 L solution). If the number of cells is lower than desired, another bag of cells can be processed.

Since all of the manipulations of the preserved hepatocytes are carried out in environmental isolation, the cell suspension remains sterile. Hydrated microcarriers also can be added aseptically to the hepatocyte suspension. The cells can then be used in artificial liver applications.

The method of establishing a target number of cells in a closed vessel and the previously used open vessel method of establishing a number of cells were directly compared by carrying out each of the methods with the same cell lots using similar equipment in the same laboratory using good manufacturing practice validation studies.

Cryopreserved porcine hepatocytes were recovered by the closed vessel method of the invention and the traditional open vessel method in order to compare the number of cells recovered by each method.

According to the traditional open vessel method, a bag of cryopreserved cells (100 mL, $2.0 \times 10^9$ viable cells) contained in a protecting medium was thawed in a water bath, preferably to a temperature of between 2° C. and 8° C., or, optionally, 30° C. and 42° C. After thawing, the bag was connected to a COBE 2991 cell processor, where the cell suspension was aseptically diluted with a DMEM culture medium (400 mL) in order to equilibrate the cells, preferably at a temperature of between 2° C. and 8° C., or, optionally, 30° C. and 42° C. The cell suspension was equilibrated aseptically in the cell processing bag in the COBE 2991 cell processor via tubing. The cell suspension was centrifuged in the cell processor at about 600 rpm for about 1.5 minutes, forming a cell pellet at the perimeter of the processing bag.

The supernatant was aspirated away from the cell pellet. A second wash was performed by adding about 400 mL of DMEM to the cells, agitating the suspension, centrifuging to form a cell pellet, and aspirating the supernatant away from the cell pellet. A DMEM culture medium (between 300 and 400 mL) was added to the cell pellet. The mixture was agitated in the cell processing bag to give a cell suspension in culture medium. The bag was sealed at the inlet tubing and cut from the cell processor and transferred to a biological hood.

In the hood, the cell suspension was poured into an open sterile bottle, the volume of cell suspension in the bottle was directly measured, and a sample for cell counting was removed. The suspension was then transferred to another centrifuge. The cells were separated from the medium by centrifuging the mixture at 380–400 rpm for 3–5 minutes. The medium was aspirated away from the cell pellet and the cells were re-suspended in saline. The cell suspension was maintained at low temperatures (e.g., between 2° C. and 8° C.) until the cells were used. From the concentration of cells (i.e., viable cells/mL) determined from the cell count and the volume, the total volume of the cell suspension was adjusted to give the appropriate total number of cells.

According to the closed vessel method, a bag of cryopreserved cells (100 mL, $2.0 \times 10^9$ viable cells) contained in the protecting medium was thawed, equilibrated by adding approximately 50 mL of DMEM medium to the bag, washed with 400 mL of DMEM medium, and resuspended in the COBE 2991 cell processor except that the cell pellet was lastly resuspended in saline and the cell suspension was aseptically transferred to the seeding vessel.

The seeding vessel was agitated gently to achieve a homogenous cell suspension while a sample was drained by gravity for cell counting in a hemacytometer. The seeding vessel was stored on ice (at temperatures between about 2° C. to 8° C.) until cell counting was completed. Prior to setting up the closed system, the tare weight of the empty seeding vessel was recorded. The seeding vessel containing the cell suspension was weighed and the weight of the cell suspension was determined by difference. The weight of the cell suspension in grams was taken as equivalent to the volume of the cell suspension in milliliters.

The total number of cells in the seeding vessel was calculated from the total volume and the cell concentration (viable cells/mL) determined from the cell counting. The volume of the cell suspension which yields $5 \times 10^9$ cells (the desired dosage in this case) was determined from the cell concentration (viable cells/mL) and the volume of cell suspension to be discarded was calculated. The volume of cell suspension to be discarded was monitored gravimetrically. Since the volume decreased significantly (i.e., more than 25 mL out of 1 L of the cell suspension was removed), saline was added to compensate for the change in volume.

Viability and recovery of cells (cryopreserved porcine hepatocytes) recovered by the closed vessel method and the open vessel method were assessed. The viability and recovery of the viable and total cells were assessed by trypan blue exclusion with 1:6 dilution and counting 2 cell samples (8 fields per hemacytometer). Comparative tests were repeated 4 times. The data summary of the two methods demonstrated a difference in viability of less than 5% between the methods, and the closed vessel method resulted in an average 2% increase in recovery of viable cells. The results indicate that the viabilities and yields of cells recovered by the two methods are comparable.

Other Embodiments

From the above description, the essential characteristics of the present invention can be ascertained. Without departing from the spirit and scope thereof, various changes and modifications of the invention can be made to adapt it to various usages and conditions. Thus, other embodiments are also within the claims.

What is claimed is:

1. A method of recovering a target number of cryopreserved mammalian cells suspended in a cryoprotective medium comprising the steps of:

thawing cryopreserved mammalian cells suspended in said cryoprotective medium;

adding a culture medium to dilute said cryoprotective medium;

washing said mammalian cells with said culture medium or saline to obtain a suspension;

transferring said suspension to a closed vessel;

removing from said closed vessel a portion of said suspension to give a remaining suspension, said closed vessel having a first sealable port from which said portion is removed;

counting a number of mammalian cells in said portion to give a cell concentration of said remaining suspension;

determining a total volume of said remaining suspension by weighing said remaining suspension in said closed vessel to give a total mass of said remaining suspension and dividing said total mass by a density to give said total volume;

calculating a total number of mammalian cells in said remaining suspension by multiplying said total volume and said cell concentration;

calculating a number of mammalian cells in excess as the difference between said total number of mammalian cells and said target number of mammalian cells; and removing from said closed vessel a portion of said remaining suspension having said number of mammalian cells in excess to give said target number of mammalian cells in said closed vessel, said closed vessel having a second sealable port from which said portion is removed.

2. The method of claim 1, wherein said mammalian cells are hepatocytes, pancreatic islets, chondrocytes, cartilage cells, neural cells, or blood cells.

3. The method of claim 1, wherein said mammalian cells are hepatocytes.

4. The method of claim 1, further comprising the step of adding an additional amount of said culture medium or saline to said remaining suspension approximately equal to said portion of said remaining suspension removed through said first or second sealable port of said closed vessel to substantially restore said total volume.

5. The method of claim 4, wherein said mammalian cells are hepatocytes, pancreatic islets, chondrocytes, cartilage cells, neural cells, or blood cells.

6. The method of claim 4, wherein said mammalian cells are hepatocytes.

7. A method of recovering preserved mammalian cells suspended in a protective medium comprising the steps of:

replacing said protective medium with a culture medium or saline to form a suspension;

transferring said suspension to a closed vessel;

removing a portion of said suspension from said closed vessel through a sealable port in said closed vessel to give a remaining suspension;

counting a number of mammalian cells in said portion to give a cell concentration of said remaining suspension;

determining a total volume of said remaining suspension in said closed vessel by weighing said remaining suspension in said closed vessel to give a total mass of said ramaining suspension and dividing said total mass by a density to give said total volume; and calculating a total number of mammalian cells in said remaining suspension by multiplying said total volume and said cell concentration.

8. The method of claim 7, wherein said mammalian cells are hepatocytes, pancreatic islets, or chondrocytes, cartilage cells, neural cells, or blood cells.

9. The method of claim 7, wherein said mammalian cells are hepatocytes.

10. A method of establishing a target number of cells in a closed vessel comprising the step of:

removing from said closed vessel a portion of cells suspended in a medium or saline to give a remaining suspension, said closed vessel having a sealable port from which said portion is removed;

determining a total volume of said remaining suspension in said closed vessel by weighing said remaining suspension in said closed vessel to give a total mass of said cell suspension and dividing said total mass by a density to give said total volume;

counting a number of cells in said portion to give a cell concentration of said remaining suspension;

calculating a total number of cells in said remaining suspension by multiplying said total volume and said cell concentration;

calculating a number of cells in excess as the difference between said first total number of cells and said target number of cells; and removing a portion of said remaining suspension having to said number of cells in excess from said sealable port of said closed vessel to give said target number of cells in said closed vessel.

11. The method of claim 10, wherein said mammalian cells are hepatocytes, pancreatic cells, chondrocytes, cartilage cells, neural cells, or blood cells.

12. The method of claim 10, wherein said mammalian cells are hepatocytes.

13. The method of claim 10, further comprising the step of adding an additional amount of said medium or saline to said remaining suspension through said sealable port of said closed vessel approximately equal to said portion of said remaining suspension removed to substantially restore said total volume.

14. The method of claim 13, wherein said mammalian cells are hepatocytes, pancreatic islets, chondrocytes, cartilage cells, neural cells, or blood cells.

* * * * *